United States Patent [19]

Rimbault

[11] Patent Number: 4,935,441
[45] Date of Patent: Jun. 19, 1990

[54] FLAVENE AND THIOFLAVENE DERIVATES, PROCESSES FOR THEIR MANUFACTURE, PHARMACEUTICAL PREPARATIONS THAT CONTAIN SUCH COMPOUNDS, AND THE USE OF THE LATTER

[75] Inventor: Christian G. Rimbault, Gran-Lancy, Switzerland

[73] Assignee: Zyma SA, Nyon, Switzerland

[21] Appl. No.: 869,458

[22] Filed: May 28, 1986

Related U.S. Application Data

[63] Continuation of Ser. No. 644,004, Aug. 24, 1984, abandoned.

[30] Foreign Application Priority Data

Aug. 31, 1983 [GB] United Kingdom ............... 8323292

[51] Int. Cl.$^5$ ............... A61K 31/415; A61K 31/355; C07D 335/04; C07D 311/04
[52] U.S. Cl. ................................ 514/432; 514/456; 549/23; 549/404; 549/405; 549/406
[58] Field of Search ............... 549/23, 404, 405, 406; 514/432, 456

[56] References Cited

PUBLICATIONS

Fatome Chem. Abst., vol. 85 (1976), 13678g.
Rene Chem. Abst., vol. 84 (1976), 17075k.
Weissenfels Chem. Abst., vol. 66 (1967), 55177f.
Eur. J. Med. Chem. Chimica Therapeutica, Jan.-Feb. 1976; 11, No. 1, p. 81-82.
Eur. J. Med. Chem. Chimica Therapeutica, Jan.-Feb. 1975, 10, No. 1, pp. 72-78.
CA72:111328u (1970) New Heterocyclic Systems.

Primary Examiner—Alan Siegel
Attorney, Agent, or Firm—Irving M. Fishman

[57] ABSTRACT

Compounds of the formula I

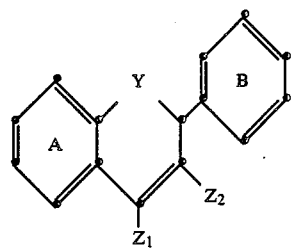

wherein rings A and B are each unsubstituted or substituted; Y is oxygen, sulfur, sulfinyl or sulfonyl; one of the symbols $Z_1$ and $Z_2$ is halogen and the other formyl; and pharmaceutically acceptable salts of such compounds that contain a salt-forming group are useful for the treatment of diseases of the respiratory tract and of liver diseases. They are prepared by methods known per se.

15 Claims, No Drawings

FLAVENE AND THIOFLAVENE DERIVATES, PROCESSES FOR THEIR MANUFACTURE, PHARMACEUTICAL PREPARATIONS THAT CONTAIN SUCH COMPOUNDS, AND THE USE OF THE LATTER

This application is a continuation of application Ser. No. 644,004, filed 8/24/84, now abandoned.

The invention relates to novel flavenes and thioflavenes and oxidized derivatives thereof, especially 3,4-disubstituted-flav-3-enes and -thio-, -sulfinyl-, and -sulfonylflav-3-enes, processes for their manufacture, pharmaceutical preparations that contain such compounds, and their use for the manufacture of pharmaceutical preparations or as pharmacologically active compounds.

The invention in particular relates to compounds of the formula I

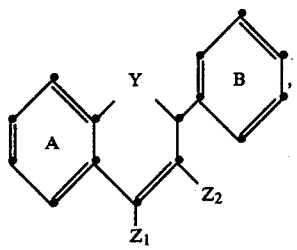

wherein rings A and B are each unsubstituted or substituted; Y is oxygen, sulfur, sulfinyl or sulfonyl; one of the symbols $Z_1$ and $Z_2$ is halogen and the other formyl; and salts, especially pharmaceutically acceptable salts, of such compounds that contain a salt-forming group, processes for the manufacture of these compounds, pharmaceutical preparations that contain such compounds, and their use for the manufacture of pharmaceutical preparations or as pharmacologically active compounds.

In case Y is sulfinyl the corresponding sulfoxide compound may exist in its α- or in its β-form.

Unless otherwise noted, "lower" radicals in the following are in particular those having up to 7, especially up to 4 and advantageously 1 or 2 carbon atoms. A substituted ring A or B as mentioned before represents a benzene ring substituted e.g. by 1, 2, 3 or 4 substituents, preferably one with 1, 2 or 3 and especially such with 1 or 2 substituents.

Hereinbefore and hereinafter, halogen is, for example, bromine or iodine, preferably fluorine and especially chlorine.

The rings A and B may optionally be substituted preferably by lower alkyl, free, etherified or esterified hydroxy, etherified mercapto, free or functionally modified carboxyl, a mono- or disubstituted amino group, acylamino, halogen, nitro, amidated sulfo, formyl and/or a methylenedioxy group. Further substituents that come into consideration are e.g. amino, di-acylamino or sulfo.

Lower alkyl groups are preferably methyl as well as ethyl, n-propyl, isopropyl, n-butyl, isobutyl, sec-butyl, tert-butyl, n-pentyl, isopentyl, neopentyl, n-hexyl, isohexyl or n-heptyl groups. Lower alkyl groups can also be substituted; such groups are for example: the nitro-lower alkyl groups, the hydroxy-lower alkyl groups, the trifluoromethyl group, the hydroxycyano-lower alkyl groups, the hydroxy- amino-lower alkyl groups, the lower-alkylthio-lower-alkyl groups, the acylalkyl groups, for example a lower-alkanoyl-lower-alkyl group, such as acetylmethyl, or a free or esterified carboxy-lower-alkyl group, for example a lower-alkoxycarbonyl-lower-alkyl group, for example methoxycarbonylethyl group, an unsubstituted or substituted imino-lower-alkyl group, such as a free or esterified hydroxyimino-lower-alkyl group, a lower-alkylimino- or unsubstituted or substituted phenylimino-lower-alkyl group, an acyloxyimino-lower-alkyl group, e.g. acetyloxyiminomethyl, di-lower-alkylimmonio-lower-alkyl, e.g. dimethylimmoniomethyl, an amino-lower-alkyl group, a mono- or di-lower-alkylamino-lower-alkyl group, or a lower-alkylene-amino-lower-alkyl group, for example a pyrrolidino- or piperidino-lower-alkyl group. A further possible substituted lower alkyl group is the lower alkyl group substituted by a 2,2-di-lower-alkyl-4,6-dioxo-1,3-dioxan-5-ylidene group, such as (2,2-dimethyl-4,6-dioxo-1,3-dioxan-5-ylidene)-methyl.

Etherified hydroxy is in particular lower alkoxy, also lower alkoxy substituted by e.g. halogen, hydroxy, mono- or di-lower-alkylamino or epoxy; further phenyloxy, phenyl-lower-alkoxy, heterocyclyloxy or heterocyclyl-lower alkoxy, such as pyridyl-oxy or -methoxy, furyl-oxy or -methoxy or thienyl-oxy or -methoxy.

Esterified hydroxy is preferably alkanoyloxy, especially lower alkanoyloxy, or benzoyloxy that optionally is substituted by hydroxy, lower alkoxy, halogen, lower alkyl and/or nitro; but can also be e.g. lower alkoxycarbonyloxy or N-lower alkylthiocarbamoyloxy.

Etherified mercapto is in particular unsubstituted or substituted lower-alkylthio, for example by free or esterified carboxyl, e.g. (S-carboxymethyl)-thio or (S-ethoxycarbonylmethyl)-thio, by halogen, e.g. trifluoromethylthio, hydroxy, amino, mono- or di-lower-alkylamino or epoxy; phenylthio or phenyl-lower-alkylthio, heterocyclylthio or heterocyclyl-lower alkylthio, e.g. 2-imidazolylthio or 2-imidazolylmethylthio.

Free or functionally modified carboxyl is for example carboxy, esterified carboxyl, especially lower-alkoxycarbonyl, such as methoxycarbonyl or ethoxycarbonyl; amidated carboxy, particularly carbamoyl which is free or mono- or disubstituted by lower alkyl, by di-lower-alkylamino-alkyl or by phenyl which is unsubstituted or for its part substituted by halogen, lower alkyl and/or lower alkoxy; and also the cyano group.

An unsubstituted or substituted amino group can be a primary, secondary or tertiary amino group. In the two last-mentioned amino groups, the nitrogen atom can carry as substituents unsubstituted or substituted aliphatic, cycloaliphatic, cycloaliphatic-aliphatic, aromatic, araliphatic, heterocyclic or heterocyclic-aliphatic hydrocarbon radicals or acyl. Two substituents taken together can however also be an unsubstituted or substituted bivalent aliphatic hydrocarbon radical, for example a lower alkylene radical or lower alkenylene radical, in which the carbon atoms of the chain can be interrupted by a heteroatom, for example oxygen, sulfur or unsubstituted or substituted nitrogen.

Secondary amino groups are in particular: lower-alkylamino, such as methylamino, ethylamino, n-propylamino, iso-propylamino or di-n-butylamino; cycloalkylamino, e.g. cyclohexylamino; phenyl-lower-alkylamino, e.g. benzylamino; phenylamino; heterocyclylamino, e.g. 2-imidazolylamino; or heterocyclyl-lower-alkylamino, e.g. 2-imidazolylmethylamino; or acylamino.

Tertiary amino groups are in particular: di-lower alkylamino, such as dimethylamino, diethylamino, di-n-propylamino or di-isopropylamino; N-cycloalkyl-N-lower-alkylamino, e.g. N-cyclopentyl-N-methylamino; N-phenyl-N-lower-alkylamino, e.g. N-methyl-N-phenylamino; or N-phenyl-lower-alkyl-N-lower-alkylamino, e.g. N-benzyl-N-methylamino; or di-acylamino.

Lower alkylamino and di-lower alkylamino groups may optionally be substituted within the lower alkyl portions, preferably by hydroxy. Advantageously the hydroxy group is separated from the amino nitrogen atom by at least 2, preferably 2 or 3, carbon atoms. Such groups are for example: 2-hydroxyethylamino, N-(2-hydroxyethyl)-N-methylamino or di-(2-hydroxyethyl)-amino.

Lower-alkyleneamino having 3 to 8, preferably 5 to 7, ring members is for example: pyrrolidino, 2,5-dimethyl-pyrrolidino, piperidino, 2-methyl-piperidino, 3-ethyl-piperidino, hexahydro-1H-azepino or octahydroazodino. Lower-alkenyleneamino, preferably having 5 to 7 ring members, is for example 2,5-dihydro-1H-pyrrol-1-yl and 1,2,3,6-tetrahydro-1-pyridyl. Mentioned as azaalkyleneamino having 6 to 8, preferably 6, ring members, in which the azanitrogen atom is unsubstituted or preferably substituted by for example lower alkyl, hydroxy-lower-alkyl, phenyl, phenyl-lower-alkyl or pyridyl or acyl, and is separated at least by 2 carbon atoms from the amino-nitrogen atom, are for example piperazino, 4-methylpiperazino, 4-(2-hydroxyethyl)-piperazino or 4-acetylpiperazino.

To be mentioned as secondary or also as tertiary amino groups in this connection are also amino groups substituted by arylamino or arylimino groups, for example phenylhydrazino or phenylazo or lower alkylamino or lower alkylimino groups, for example methylhydrazino or methylazo.

Acylamino is preferably lower-alkanoylamino, such as acetylamino, or benzoylamino, which can be substituted in the phenyl ring for example with halogen, nitro, lower alkyl and/or lower alkoxy.

Di-acylamino is e.g. dilower alkanoylamino, such as diacetylamino, or dibenzoylamino which optionally is substituted in the phenyl rings e.g. by halogen, lower alkyl, lower alkoxy and/or nitro.

Amidated sulfo is preferably sulfamoyl, N-lower alkylsulfamoyl, e.g. N-methylsulfamoyl, N,N-dilower alkylsulfamoyl, e.g. N,N-dimethylsulfamoyl, or N-phenylsulfamoyl optionally substituted by e.g. lower alkyl, halogen, lower alkoxy and/or nitro in the phenyl ring.

"Heterocyclyl" when referred to above or hereinafter in connection with organic groups or radicals, e.g. within expressions like heterocyclyloxy, heterocyclyl-lower alkoxy, heterocyclylthio, heterocyclyl-lower alkylthio, heterocyclylamino or heterocyclyl-lower alkylamino, is e.g. a monocyclic heterocyclic radical having 3 to 8, preferably 5 to 8 and advantageously 5 or 6 ring members, which is preferably bonded by a ring carbon atom to the moiety that it is joined with. It contains e.g. 0 to 4, preferably 1, 2 or 3 double bonds and is advantageously of aromatic character; in the latter case it is named "heteroaryl".

Usually "heterocyclyl" contains 1 to 4, identical or different, hetero atoms as ring members, especially nitrogen, oxygen and/or sulfur atoms. Preferred are aza-, oxa-, thia-, thiaza-, oxaza-, diaza-, triaza- or tetraza- monocycles. Monocyclic "heterocyclyl" may optionally contain e.g. 1 or 2, preferably 1, fused benzo rings.

Monocyclic five-membered heteroaryl is e.g. pyrryl, pyrazolyl, imidazolyl, triazolyl, tetrazolyl, furyl, thienyl, isoxazolyl, oxazolyl, isothiazolyl or thiazolyl, while monocyclic six-membered heteroaryl is e.g. pyridyl, pyridazinyl, pyrimidinyl, pyrazinyl or triazinyl. Monocyclic heteroaryl fused with one benzo ring is e.g. indolyl, isoindolyl, benzimidazolyl, benzofuranyl, benzothienyl, benzothiazolyl, benzoxazolyl, quinolinyl or isoquinolinyl. Such with two fused benzo rings is e.g. dibenzofuranyl. Monocyclic five- or six-membered heterocyclyl being not of aromatic character is preferably the partially saturated corresponding heteroaryl, e.g. dihydropyrryl, such as 4,5-dihydro-3-pyrrolyl, dihydrooxazolyl, such as 4,5-dihydro-2-oxazolyl, or 1,2-dihydropyrimidinyl, such as 1,2-dihydro-4-pyrimidinyl or tetrahydro-triazinyl, such as tetrahydro-1,2,4-triazin-3-yl.

Heterocyclyl radicals are unsubstituted or may be substituted, such as mono- or poly-substituted, such as, especially, disubstituted by hydroxy, lower alkoxy, lower alkanoyloxy, halogen, mercapto, lower alkylthio, phenylthio, lower alkyl, hydroxy-lower alkyl, lower alkoxy-lower alkyl, carboxy-lower alkyl, optionally N-lower alkylated amino-lower alkyl, amino, lower alkylamino, di-lower alkylamino, lower alkyleneamino or acylamino, such as lower alkanoylamino, carboxy, esterified carboxy, such as lower alkoxycarbonyl, optionally substituted carbamoyl, such as N-mono- or N,N-di-lower alkylated carbamoyl, cyano, sulfo or sulfamoyl; phenyl optionally substituted by lower alkyl, nitro, lower alkoxy and/or by halogen; cycloalkyl, nitro, oxo and/or oxido.

Phenyl radicals when referred to within expressions like phenyloxy, phenyl-lower alkoxy, phenylthio, phenyl-lower alkylthio, phenylamino or phenyl-lower alkylamino are unsubstituted or may be substituted in exactly the same way as described above for heterocyclyl radicals, with the exception of oxo and oxido substituents which are not suitable in case of phenyl.

Lower alkoxy is for example methoxy, ethoxy, n-propoxy, isopropoxy, n-butoxy or tert-butoxy.

Phenyl-lower alkoxy is for example benzyloxy, 2-phenylethoxy or diphenylmethoxy.

Alkanoyloxy is especially lower alkanoyloxy such as formyloxy, acetoxy, propionyloxy, butyryloxy, isobutyryloxy, pivaloyloxy or valeroyloxy. But alkanoyloxy can also be e.g. palmitoyloxy.

Lower alkoxycarbonyloxy is for example methoxycarbonyloxy or ethoxycarbonyloxy.

N-Lower alkylthiocarbamoyloxy is for example N-methylthiocarbamoyloxy.

Lower alkylthio is for example methylthio, ethylthio, n-propylthio, isopropylthio, n-butylthio or tert-butylthio.

Phenyl-lower alkylthio is for example benzylthio or 2-phenylethylthio.

Cycloalkyl is preferably $(C_3-C_8)$cycloalkyl, e.g. cyclohexyl.

The compounds of the formula I possess valuable pharmacological properties. They, for example, stimulate the mucociliary transport in bronchia, and they modify the secretion of the viscoelasticity of mucus produced by bronchial and tracheal glands. These properties make the compounds useful for the treatment of diseases of the respiratory tract, as for example chronic bronchitis, in mammals The stimulation of mucociliary transport can be demonstrated with pharmacological model of frog oesophagus. In this system, the speed of transport of particles by the ciliated epithelium of frog oesophagus is measured according to Puchelle et al. [Bull. Physio. Path. resp. 12, 771–779 (1976)].

By adding solutions of compounds to be tested on the frog oesophagus an increase in the speed of transport is measured. This effect appears when using solutions of compounds of formula I with a concentration of only $10^{-3}$–$10^{-4}$ M or less.

The modification of viscoelasticity of mucus samples caused by compounds of formula I can be measured with a microrheometer according to C. Marriott [Advances in experimental Medicine and Biology, 144, 75–84 (1981)].

The mucus is obtained from fresh pig's stomach scrapings and is purified biochemically before use. The test compounds are dissolved in specific solvents, distilled water, phosphate buffer, methanol aqueous mixture, or in DMSO (dimethylsulfoxide). 50 mg aliquotes of mucus with 5–10 $\mu$l of the test solution are added. The samples are mixed, centrifuged and incubated for 30 min. for interaction to take place. The samples are then loaded into the cell of an oscillating sphere magnetic microrheometer and a 200 $\mu$m iron sphere is placed centerally in the sample which is allowed 5 minutes for relaxation to take place. The rheological behaviour is evaluated at 25° C. over the frequency range of 0.1 to 20 Hz. The elastic modulus $G'$ of mucus is changed, preferably reduced, but also enlarged, by using the compounds of formula I.

The mucoregulators properties of the compounds of formula I can be evaluated by the use of the "Ussing Chamber Method" described in Respirat. Environ. Exercice Physiol. 49, 1027–1031 (1980).

In this method pieces of pig trachea are keptalive in physiological saline medium. The outlets of tracheal glands are observed via a light microscope. The mucus output is triggered either by electric stimulation or by addition of pilocarpineto the incubation medium. The number and the surface of mucus hillocks are recorded via a video tape recorder. The addition of the compounds of formula I in the incubation medium at a concentration of only $10^{-4}$ M or less modifies the number and the surface of hillocks reflecting a change in mucus secretion.

The compounds of formula I also have properties of preventing the hepatic necrosis and of immunomodulation.

The hepatic antinecrotic properties of these substances can be demonstrated by the galactosamine hepatitis test in the rat and the carbontetrachloride hepatitis test in the mouse. The galactosamine hepatitis in the rat is a well-known model to faithfully reproduce the morphological and biochemical changes of the human viral hepatitis [K. Decker et al., Adv. Enzyme regul. 11, 205 (1973)].

Rats treated intraperitoneally or orally with doses of the compounds of formula I varying from 10 to 200 mg/kg are protected from the hepatic necrosis induced with galactosamine or carbontetrachloride. The hepatic effect is assessed by dosage of plasma transaminases and by measuring the sleeping time induced by pentobarbital which reflects liver function.

The immunomodulation properties of these substances can be demonstrated by a battery of tests classically used in immunology:

(a) humoral immunity test: production of antibodies against the bovine albumine in the mouse. Compounds of formula I, administered at a dose of 10 to 100 mg/kg, 15 minutes after the antigen (bovine albumine), stimulate the antibody production against this antigen, as measured 15 to 28 days later by the passive hemagglutination technique.

(b) cellular immunity test: delayed hypersensitivity reaction to sheep red blood cells in mice. Compounds of formula I administered at a dose of 10 to 100 mg/kg by subcutaneous route at the same time as the antigen stimulate the delayed hypersensitivity reaction triggered off 21 days later by a subcutaneous injection of the antigen.

(c) cytotoxicity test of mice macrophages against tumoral cells. The macrophages collected from mice having been treated by doses of 10 to 100 mg/kg of compounds of formula I, have a stimulated cytotoxicity against tumoral target cells.

These tests establish that the three main processes involved in the immunological defence (humoral immunity, cellular immunity and macrophages) are modified by the action of compounds of formula I and demonstrate their immunoundulating properties.

These various properties particularly designate the compounds of formula I for the treatment in mammals of acute and chronic diseases induced by viruses, toxins or alcohol. As a matter of fact, during these diseases, the impairment of the hepatic functions results essentially from the hepatic necrosis. This alterations can be diminished by the new substances.

The stimulation of the immunologic defences induced by these substances is useful for the treatment in mammals of the acute and chronic viral hepatitis and also for the treatment of all cases when there is an alteration of immunologic defence reactions such as repeating bacterial or viral infections or carcinogenous diseases. In the latter case, the interest of the substances is specifically demonstrated by the activation of cytotoxic effect of macrophages for tumoral cells.

Compounds of formula I are also able to diminish an increased microvascular permeability and therefore are very potent antioedamators agents in mammals.

Increased microvascular permeability with generalized oedema can be induced in rats by administration of galactosamine and dextran.

At doses administered parenterally or orally varying from 10 to 500 mg/kg compounds of formula I prove to be able to reduce the oedema as measured by the reduction in the accumulation of $I^{125}$ labelled albumine in paws of animals which receive previously an i.v. injection of $I^{125}$ albumine. This measurement is an estimation of the micro-vascular permeability as reported by O. P. Gulati et al., Archives Int. de Pharmacodynamie et de Thérapie 263, pp. 272–287 (1983).

Preferred are the compounds of formula I, wherein rings A and B are each optionally substituted by 1, 2, 3, or 4 substituents selected from the group comprising lower alkyl, hydroxy, lower alkoxy, lower alkanoyloxy, lower alkylthio, amino, lower alkylamino, di-lower alkylamino, acylamino, halogen, carboxy, lower alkoxycarbonyl, carbamoyl, N-mono-or N,N-di-lower alkylcarbamoyl, cyano, nitro, sulfo, sulfamoyl, N-lower-alkyl-, N,N-di-lower-alkyl- or N-phenylsulfamoyl, formyl and methylenedioxy; Y is oxygen, sulfur, sulfinyl or sulfonyl; one of the symbols $Z_1$ and $Z_2$ is halogen and the other formyl; and salts of such compounds that contain a salt-forming group.

More especially preferred novel compounds are those of the formula I, wherein rings A and B are each optionally substituted by 1 or 2 substituents comprising halogen, lower alkyl, hydroxy, lower alkoxy, esterified hydroxy, unsubstituted or lower-alkyl- and/or phenyl-substituted amino, acylamino, formyl or carboxy; Y is oxygen or sulfur; one of the symbols $Z_1$ and $Z_2$ is chlorine or fluorine and the other formyl; and salts, especially pharmaceutically acceptable salts, of such compounds that contain a salt-forming group.

Most especially preferred are the compounds of formula I, wherein rings A and B are each optionally substituted by 1, 2 or 3 substituents selected from the group comprising lower alkyl, hydroxy, lower alkoxy, lower alkanoyloxy, lower alkylamino, di-lower alkylamino, lower alkanoylamino, halogen, formyl and carboxy; Y is oxygen or sulfur; one of the symbols $Z_1$ and $Z_2$ is chlorine or fluorine and the other is formyl; and pharmaceutically acceptable salts of such compounds that contain a salt-forming group.

In general, preferred are the compounds of formula I, wherein Y represents oxygen or sulfur, and especially preferred are those, wherein Y is oxygen.

Another preferred embodiment of this invention are the compounds of formula I, wherein Y represents oxygen, sulfinyl or sulfonyl.

One further preferred embodiment of this invention are the compounds of formula I wherein $Z_2$ is formyl and $Z_1$ is halogen.

Another preferred embodiment of this invention are the compounds of formula I wherein $Z_1$ is formyl and $Z_2$ is halogen.

Greatly preferred novel compounds are those of the formula I, wherein rings A and B are each optionally substituted by 1 or 2 substituents comprising halogen, lower alkyl, hydroxy, lower alkoxy, esterified hydroxy, amino, lower-alkylamino, di-lower-alkylamino, lower-alkanoylamino, formyl or carboxy; Y is oxygen or sulfur; $Z_1$ is chlorine or fluorine and $Z_2$ is formyl; and salts, especially therapeutically applicable salts, of such compounds that contain a salt-forming group.

The compounds specifically preferred are: 4-chloro-3-formyl-flav-3-ene, 4-chloro-3-formyl-thioflav-3-ene, 4-chloro-3-formyl-5-hydroxy-flav-3-ene, 4-chloro-6-fluoro-3-formyl-flav-3-ene, 6-carboxy-4-chloro-3-formyl-flav-3-ene, 4-chloro-3-formyl-6-methyl-thioflav-3-ene, 4-chloro-7-fluoro-3-formyl-flav-3-ene, 4-chloro-7-N,N-dimethylamino-3-formyl-1-flav-3-ene, 7-acetylamino-4-chloro-3-formyl-flav-3-ene, 4-chloro-3'-fluoro-3-formyl-flav-3-ene, 4-chloro-3-formyl-4'-hydroxy-flav-3-ene, 4-chloro-3-formyl-4'-formyloxy-flav-3-ene, 4-chloro-5,7-di-methoxy-3-formyl-flav-3-ene, 4-chloro-3,8-diformyl-5,7-dimethoxy-flav-3-ene, 4-chloro-3-formyl-5,6,7-trimethoxy-flav-3-ene, 4-chloro-6-N,N-dimethylamino-3-formyl-flav-3-ene, 4-fluoro-3-formyl-flav-3-ene, 4-chloro-3-formyl-8-methoxy-thioflav-3-ene, 4-chloro-4'-fluoro-3-formyl-thioflav-3-ene, 4-chloro-2'-fluoro-3-formyl-thioflav-3-ene and 4-chloro-3-formyl-7-methoxy-thioflav-3-ene.

Above all are preferred the compounds of formula I described in the examples and pharmaceutically acceptable salts thereof.

The compounds of the present invention are obtained according to processes known per se.

Compounds of the formula I, wherein $Z_1$ is halogen and $Z_2$ is formyl, and salts of such compounds that have a salt-forming group can be manufactured, for example, by reacting a compound of the formula II

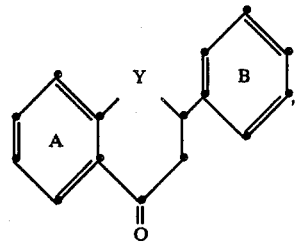

in which A, B and Y have the meanings given under formula I, with phosphorous oxyhalide, $PO(Hal)_3$, and a formamide of the general formula III

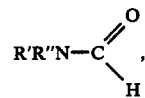

in which R' and R" is hydrogen, lower alkyl or phenyl, or in which R' and R" are together lower alkylene; and/or, if desired, converting a resulting compound of the formula I into another compound of the formula I, and/or, if desired, converting a resulting salt into the free compound or into another salt, and/or, if desired, converting a resulting free compound of the formula I having a salt-forming group into a salt, and/or, if desired, resolving a mixture of isomers or racemates obtained into the single isomers or racemates, and, if required, resolving a racemate obtained into the optical antipodes.

A phosphorous oxyhalide $PO(Hal)_3$ hereinbefore and hereinafter is, for example, phosphorous oxybromide or preferably phosphorous oxychloride.

In a compound of the formula III lower alkyl is for example methyl, and lower alkylene as R' and R" taken together for example pentylene. The Vilsmeier-reaction can be performed for example according to HoubenWeyl, 4th Edition, Vol. 7/1, pp. 29–36, and Chem. Ber. 60 (1927), p. 121. Most suitable as formylating agent is dimethylformamide. As further modifications, suitable formylating agents are e.g. formamide, formylpiperidine and formylmonomethyl-aniline. The phosphorous oxychloride used here can be successfully replaced in some cases by e.g. phosgene or thionykhloride according to Bbhme and Viehe, Adv. in Org. Chem. Vol. 9, I, pp. 229–232. This reaction of Arnold-Vilsmeier type is described in detail e.g. in Adv. in Org. Chem., Vol. 9, I, pp. 274–298.

Compounds of the formula I, wherein $Z_1$ is formyl and $Z_2$ is halogen, can be produced, for example, by reacting a compound of the formula IIa

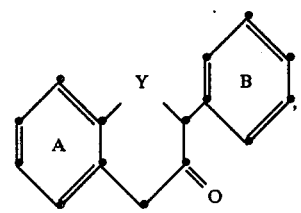

wherein A, B and Y have the meanings given under formula I, with a compound of the formula III, wherein R' and R" are defined as above, in essentially the same manner as described above for the reaction of a compound of the formula II with a compound of the formula III.

The starting materials of the formulae II, IIa and III are known or, if novel, can be prepared by methods known per se.

Thus, compounds of the formula II, wherein Y is sulfur or oxygen and A and B have the meanings given under the formula I, can be obtained e.g. by cyclisation of a compound of the formula VIII

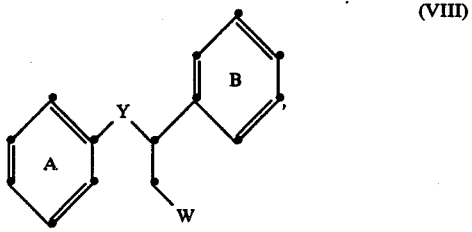

(VIII)

wherein W is carboxy, or a reactive derivate thereof, such as an acid halide, for example an acid chloride or acid bromide or an anhydride, Y is sulfur or oxygen and A and B have the meanings given under formula I, using phosphorous oxychloride, preferably under an inert gas atmosphere, for example under a nitrogen atmosphere.

Further, as a process variant, it is also possible to manufacture compounds of the formula I, wherein Y is sulfur or oxygen, $Z_1$ is halogen and $Z_2$ is formyl, directly from compounds of the formula VIII by treating the latter with phosphorous oxyhalide, for example phosphorous oxychloride, and subsequently or simultaneously with a formamide of the formula III in an one-pot-reaction.

Compounds of the formula II, wherein Y is oxygen or sulfur, and A and B have the meanings given under formula I, can be obtained further by cyclisation of chalcones of the formula IX

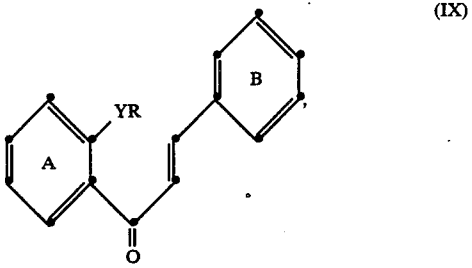

(IX)

wherein Y is oxygen or sulfur, R is a hydroxy- or mercapto-protecting group, such as acyl, for example acetyl, or, in case Y is oxygen, hydrogen, and A and B have the meanings given under formula I.

Compounds of formula IX can be prepared e.g. by reacting an optionally protected 2-hydroxy- or 2-mercaptoacetophenone with benzaldehyde preferably under acidic conditions, for example in the presence of an inorganic acid, such as hydrochloric acid, or a lewis acid, for example aluminium trichloride or boron trifluoride, according to Dhar, The Chemistry of Chalcones and Related Compounds, New York 1981, pp. 8–9.

Compounds of the formula IIa, wherein Y is sulfur, can be produced for example by condensation (Dieckmann) of a 2-carboxymethylthiophenylacetic acid and hydrolysis of the intermediate 3-acetoxy-thioflav-3-ene preferably in acidic medium for example with an inorganic acid, such as hydrochloric acid, or with an organic acid, such as acetic acid, according to Can. J. Chem. 60, 243 (1982).

Furthermore, compounds of the formula IIa, wherein Y is oxygen, can be prepared for example by oxidation of the corresponding trans-flavan-3-ol using dimethylsulfoxide and diethylcarbodiimide as oxidizing agent and pyridinium trifluoroacetate as a proton source according to Austr. J. Chem. 29, 2485 (1976).

Compounds of the formula IIa, wherein Y is oxygen, A is phenylene and B is phenyl can be further manufactured in a photoreaction starting from 4-phenylchroman-3-one. By passing a transient spirocyclohexadienone structure the desired compound of the formula IIa is formed due to a 1,3-sigmatropic shift according to J. Chem. Soc. Chem. Commun. 1975, 58 and J. Org. Chem. 43, 303 (1978).

Compounds of the formulae II and IIa, wherein Y is sulfinyl and A and B have the meanings defined under formula I, can be produced e.g. by oxidation of a corresponding compound of the formula II or IIa, wherein Y is sulfur and A and B have the meanings defined under the formula I, in the usual manner. The oxidation to sulfinyl can be effected for example by inorganic peracids, such as peracids of mineral acids, for example periodic acid or persulfuric acid; organic peracids, such as percarboxylic or persulfonic acids, for example performic, peracetic or trifluoroperacetic acid, m-chloroperbenzoic acid or p-toluenepersulfonic acid; by mixtures consisting of hydrogen peroxide and acids, for example mixtures of hydrogen peroxide and acetic acid.

Often the oxidation is carried out in the presence of suitable catalysts, for example acids, which are suitable as catalysts, such as optionally substituted carboxylic acids, for example acetic or trifluoroacetic acid, or e.g. oxides of transition metals, such as the oxides of the elements of the auxiliary group VII, for example vanadium, molybdenum or tungsten oxide, or oxides of subgroup 6A of the periodic table, e.g. selenium dioxide.

Compounds of the formulae II and IIa, wherein Y is sulfonyl and A and B have the meanings defined under formula I, can be obtained e.g. by oxidation of a corresponding compound of the formula II or IIa, wherein Y is sulfur or sulfinyl and A and B have the meanings defined under the formula I, for example with dinitrogentetroxide as a catalyst, in the presence of oxygen at low temperature using the same oxidation means as just described above for the oxidation to sulfinyl, but usually taking an excess of them.

On the contrary, compounds of the formulae II and IIa, wherein Y is sulfinyl or sulfonyl, can be reduced to compounds of the formulae II and IIa, wherein Y is sulfur. A suitable reduction means is for example catalytically activated hydrogen using nobel metals or oxides thereof as catalysts, such as palladium, platinum or rhodium or oxides thereof respectively, which are optionally distributed on a suitable carrier, such as charcoal or barium sulfate.

Furthermore, reducing metal cations, such as tin(II), lead(II), copper(I), manganese(II), titanium(II), vanadium(II), molybdenum(III) or tungsten(III) compounds; hydrogen halides, such as hydrogen chloride, bromide or iodide; hydrides, such as complex metal hydrides, for example lithium aluminium, sodium boron or tributyltin hydride; phosphorous compounds, such as phosphorous halides, for example phosphorous trichloride or -tribromide, phosphorous pentachloride or -oxychloride;

phosphines, such as triphenylphosphine; or phosphorous pentasulfide-pyridine; or sulfur compounds, such as mercaptanes, thioacids, thiophosphorous acids or dithiocarboxylic acids, dithionites or sulfur complexes, such as the iodine-pyridine-sulfurdioxide complex, can be used as reducing agents.

It is also possible in essentially the same manner as described above for compounds of the formulae II and IIa to convert compounds of the formula I, wherein Y is sulfur, sulfinyl or sulfonyl, and A, B, $Z_1$ and $Z_2$ have the meanings given under the formula I, into other compounds of the formula I, wherein Y is sulfinyl, sulfonyl or sulfur, provided that functional groups eventually present which are sensitive to the above-described oxidation and reduction methods, for example formyl, are protected by conventional protecting groups.

Generally, in starting materials of the formulae II, IIa, IV, VIII and IX, as well as in compounds of the formula I to be converted into another compound of the formula I, functional groups present, especially formyl, carboxy, amino, hydroxy and mercapto groups, and also sulfo groups, are optionally protected by conventional protecting groups that are customary in preparative organic chemistry. Protected formyl, carboxy, amino, hydroxy, mercapto and sulfo groups are those that can be converted under mild conditions into free formyl, carboxy, amino, hydroxy, mercapto and sulfo groups without the molecular framework being destroyed or other undesired side reactions taking place.

The purpose of introducing protecting groups is to protect the functional groups from undesired reactions with reaction components and thus prevent them of being removed or converted into a derivative. On the other hand, reaction components can be consumed or bonded, in an undesired manner by reaction with an unprotected functional group and are then no longer available for the actual reaction. The choice of protecting groups for a particular reaction depends on the nature of the functional group to be protected (carboxy group, amino group etc.), the structure and stability of the molecule of which the substituent is the functional group, and the reaction conditions.

Protecting groups that meet these conditions and their introduction and removal are known and are described, for example, in J. F. W. McOmie, "Protective Groups in Organic Chemistry", Plenum Press, London, New York 1973, T. W. Greene, "Protective Groups in Organic Synthesis", Wiley, New York 1981, and also in "The Peptides", Vol. I, Schroeder and Luebke, Academic Press, London, New York 1965, as well as in Houben-Weyl, "Methoden der Organischen Chemie", Vol. 151, Georg Thieme Verlag, Stuttgart, 1974.

Compounds of the formula I, wherein $Z_1$ is halogen and $Z_2$ is formyl, and salts of such compounds that have a salt-forming group, can also be produced e.g. by reaction of a compound of formula IV

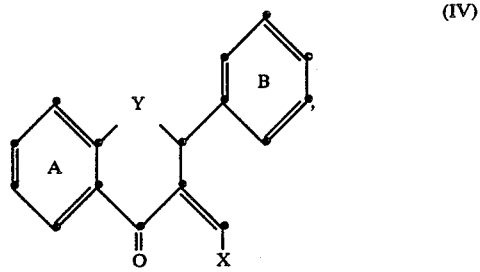

in which A, B and Y have the meanings given under formula I, and in which X is an unsubstituted or substituted amino group, with phosphorous oxyhalide, PO(-Hal)$_3$, or with phosgene, a thionylhalide such as thionylchloride, a phosphorous pentahalide such as phosphorous pentachloride, a trihaloacetylhalide such as trichloroacetylchloride or an arylsulfonylhalide, such as p-toluenesulfonylchloride, according to Buhme and Viehe, Adv. in Org. Chem., Vol. 9, I, pp. 289–300.

In a compound of the formula IV an unsubstituted or substituted amino group has the meanings as earlier defined above under formula I.

The reaction of a compound of the formula IV with e.g. phosphorous oxyhalide is carried out in a conventional manner, advantageously in an inert solvent, such as a halogenated hydrocarbon, for example dichloromethane.

The starting materials of the formula IV can be prepared by methods known per se.

Thus, for example the reaction of a compound of the formula II, in which A, B and Y have the meanings given under formula I, with a compound of the formula IIIa,

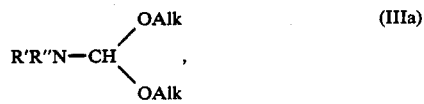

wherein Alk is lower alkyl, such as methyl or ethyl, or benzyl, and R' and R" have the meanings as defined under the formula III, yields a compound of the formula IV, in which A, B and Y have the meanings given under the formula I.

Compounds of the formula I obtained can be converted into other compounds of the formula I in a manner known per se.

Thus, compounds of the formula I, wherein one of the symbols $Z_1$ and $Z_2$ is fluoro and the other is formyl, can be obtained e.g. from a corresponding compound of formula I, wherein one of the symbols $Z_1$ and $Z_2$ is chloro, bromo or iodo and the other is formyl, in a substitution reaction with an alkali metal or alkaline-earth metal fluoride, especially cesiumfluoride, preferably in an aprotic solvent, such as dimethylformamide.

Furthermore, it is possible within the scope of the definition of the compounds of the formula I to convert compounds obtained in customary manner into other compounds of the formula I by modifying, introducing or splitting off suitable substituents within the rings A and B.

Free carboxy groups can be esterified in customary manner, for example by reacting with a corresponding alcohol, advantageously in the Presence of an acid, such as a mineral acid, for example sulfuric acid or hydrochloric acid, or in the presence of a water-binding agent, such as dicyclohexylcarbodiimide, or by reacting with a corresponding diazo compound, for example diazomethane. Esterification can also be carried out by reacting a salt, preferably an alkali metal salt, of the acid with a reactive esterified alcohol, for example a corresponding halide, such as a chloride.

Free carboxy groups can be amidated in customary manner, for example by reacting with ammonia or with a primary or secondary amine, advantageously in the presence of a water-binding agent, such as dicyclohexylcarbodiimide, or by converting the carboxy group into a halocarbonyl group, for example a chlorocarbonyl group, and then reacting with ammonia or a primary or secondary amine.

In compounds that contain an esterified carboxy group, the latter can be converted into a free carboxy group in customary manner, for example by hydrolysis, preferably in the presence of strong bases, such as an alkali metal hydroxide, for example sodium or potassium hydroxide, or strong acids, for example a strong mineral acid, such as a hydrohalic acid, for example hydrochloric acid, or sulfuric acid.

In compounds having an esterified carboxy group as substituent, the latter can be converted into the corresponding carbamoyl group in customary manner, for example by ammonolysis or aminolysis with ammonia or a primary or secondary amine.

Compounds having a carbamoyl group as substituent can be dehydrated to form the corresponding cyano compounds in customary manner, for example by the action of dehydrating agents, such as phosphorous pentoxide, phosphorous oxychloride or trifluoroacetic acid anhydride, preferably at elevated temperatures.

In compounds having an esterified carboxy group as substituent, the esterified carboxy group can be converted into a cyano group in customary manner, for example by the action of an organic aluminium amide compound, such as a di-lower alkylaluminium amide compound, for example diethylaluminium amide.

Compounds containing a cyano substituent can be hydrolysed to the corresponding carbamoyl compounds or directly to the carboxy compounds in customary manner, for example in the presence of concentrated aqueous mineral acids or alkali metal hydroxides.

Compounds having a cyano group as substituent can be alcoholysed to form corresponding compounds having esterified carboxy groups in customary manner, for example by the addition of alcohols in the presence of an anhydrous acid, such a hydrogen chloride, and subsequent hydrolysis of the resulting imido ester.

Compounds of the formula I containing a primary or secondary amino group as substituent can be converted into compounds of the formula I which contain a tertiary amino group by introducing a substituent, for example an optionally substituted lower alkyl group, such as methyl or benzyl, in customary manner, for example using a corresponding reactive esterified alcohol, such as a corresponding halide, for example chloride or bromide, or a diazoalkane, for example diazomethane.

Compounds that carry in the rings A and B a lower alkylthio group, for example a methylthio group, can be converted into the sulfur-free compounds by treating with suitable desulfurating agents, for example Raney nickel, in a suitable solvent, for example dioxane.

In compounds of the formula I which carry at least one hydroxy as substituent of the rings A and/or B, hydroxy may be etherified in customary manner. The reaction to form the corresponding ethers is carried out, for example, in the presence of bases, such as alkali metal hydroxides or carbonates, for example sodium hydroxide or potassium carbonate, by means of di-lower-alkyl-sulfates or lower alkyl halides or in the presence of a dehydrating agent, for example dicyclohexylcarbodiimide, by means of lower alkanols.

In compounds of the formula I in which an aliphatically or cycloaliphatically bonded hydroxy or mercapto group is present, for example as substituent of the rings A and/or B, this group may be etherified in customary manner. Suitable etherifying agents are e.g. diazo compounds, such as unsubstituted or substituted diazo-lower alkanes, for example diazomethane. Further suitable etherifying agents are esters of corresponding alcohols, especially those with strong inorganic or organic acids, such as mineral acids, e.g. hydrohalic acids, such as hydrochloric acid, and also sulfuric acid, or strong sulfonic acids, such as lower alkanesulfonic acids which are unsubstituted or substituted e.g. by lower alkyl, such as methyl, for example methanesulfonic acid, trifluoromethanesulfonic acid or p-toluenesulfonic acid. Such esters are for example lower alkyl halides, for examples methyl iodide, or sulfates, such as dimethyl sulfate.

Compounds of the formula I in which at least one of the rings A and B is substituted by esterified hydroxy and/or mercapto can be obtained by treating a compound of the formula I in which at least one of the rings A and B is substituted by hydroxy and/or mercapto with an acylating agent introducing the desired acyl radical. Such agent are, for example, optionally substituted lower alkanecarboxylic acids, optionally substituted benzoic acids or reactive derivatives thereof, such as anhydrides or acid halides, for example acid chlorides, or hydrohalic acids, especially in the form of reactive esters, for example thionylchloride and phosphorous tribromide.

Conversely, compounds of the formula I in which at least one of the rings A and B is substituted by esterified hydroxy and/or mercapto can be converted into compounds of the formula I in which at least one of the rings A and B is substituted by hydroxy and/or mercapto. The conversion to hydroxy and/or mercapto is carried out, for example, by alcoholysis with a lower alkanol, for example methanol or ethanol, or preferably by hydrolysis, such as base-catalysed hydrolysis, for example in the presence of sodium hydroxide.

Lower alkoxy and phenoxy groups as well as lower alkylthio and phenylthio groups can be converted to free hydroxy and free mercapto groups by mineral acids, e.g. hydrohalic acids, such as hydroiodic acid, or Lewis acids, for example aluminium trichloride.

As in the manufacturing processes, when carrying out the additional steps, care must be taken that undesired side reactions which may result in the conversion of additional groups do not occur.

The reactions described above may be carried out simultaneously or in succession, as desired, and also in any sequence. If necessary, they are carried out in the presence of diluents, condensation agents and/or catalytically active agents, at reduced or elevated temperature, in a closed vessel under pressure and/or in an inert gas atmosphere.

Acid addition salts of compounds of the formula I are obtained in customary manner, for example by treating with an acid or a suitable anion exchanger. The resulting salts can be converted into the free compounds in a manner known per se, for example by treating with a suitable basic agent, for example a metal hydroxide, ammonia or a hydroxyl ion exchanger. On the other hand, compounds having an acidic group, e.g. a carboxy or a phenolic hydroxy group can be converted into an alkali metal salt in a manner known per se by treating, for example, with an alkali metal hydroxide. The free compounds can be obtained by treating with an acid.

Salts of compounds of the formula I are especially pharmaceutically acceptable non-toxic salts, such as those of compounds of the formula I with acidic groups, for example with a free carboxyl or sulfo group. Such salts are especially metal or ammonium salts, such as alkali metal or alkaline earth metal salts, for example sodium, potassium, magnesium or calcium salts, as well as ammonium salts, which are formed with ammonia or suitable organic amines. There come into consideration for the salt formation especially aliphatic, cycloaliphatic, cycloaliphatic-aliphatic or araliphatic primary, secondary or tertiary mono-, di- or poly-amines, as well as heterocyclic bases, such as lower alkylamines, for example di- or tri-ethylamine, hydroxy-lower alkylamines, for example 2-hydroxyethylamine, bis-(2-hydroxyethyl)-amine or tris-(2-hydroxyethyl)-amine, basic aliphatic esters or carboxylic acids, for example 4-aminobenzoic acid, 2-diethylaminoethyl ester, lower alkyleneamines, for example 1-ethylpiperidine, cycloalkylamines, for example dicyclohexylamine, or benzylamines, for example N,N'-dibenzylethylenediamine.

Compounds of formula I having a basic group, e.g. an amino group, may form acid addition salts, for example with inorganic acids, such as hydrochloric acid, sulfuric acid or phosphoric acid, or with suitable organic carboxylic or sulfonic acids, for example acetic acid, succinic acid, fumaric acid, tartaric acid, methanesulfonic acid and p-toluenesulfonic acid. In the presence of several acidic or basic groups, mono- or poly-salts may be formed. Compounds of the formula I having an acidic group, for example a free carboxy group, and a basic group, for example an amino group, may also be present in the form of inner salts, i.e. in zwitterionic form, or a part of the molecule may be present in the form of an inner salt and another part in the form of a normal salt.

The pharmaceutically acceptable salts mentioned above are preferred. For isolation or purification it is also possible to use other salts than the therapeutically acceptable salts. Owing to the close relationships between the novel compounds in free form and in the form of their salts, hereinbefore and hereinafter there shall optionally be understood by free compounds and salts, where appropriate with regard to meaning and purpose, also the corresponding salts and free compounds, respectively.

The compounds of the formula I, including their salts, can also be obtained in the form of their hydrates or can include the solvent used for their crystallisation.

The compounds of the formula I have at least one asymmetric center at the carbon atom 2. Therefore they can be found as R- or S-enantiomers as well as a racemate. The present invention is intended to include all these forms, also those further stereoisomers and mixtures of at least two stereoisomers, for example a diastereomeric mixture or enantiomeric mixture, such as a racemate, which are possible if one or more other asymmetric centers are present within the molecule.

Starting materials and end products that are isomeric mixtures can be separated into the individual isomers by methods known per se, for example by fractional distillation, crystallisation and/or chromatography. Racemic products can be separated into the optical antipodes, for example by chromatography and/or separation of their diastereoisomeric salts, for example by fractional crystallisation of the d- or l-camphor-sulfonates, -mandelates, -tartrates or -dibenzoyltartrates.

The invention relates also to modifications of the present process, according to which an intermediate obtainable at any stage of the process is used as starting material and the remaining process steps are carried out, or the process is discontinued at any stage, or according to which a starting material is formed under the reaction conditions, or in which a starting material is used in the form of a salt or a reactive derivative. The invention also comprises novel intermediates resulting therefrom.

In the process of the present invention the starting materials used are preferably those which result in the compounds described at the beginning as being especially valuable.

The starting materials used in the process for the manufacture of the compounds of the present invention are known or, if they are novel, they can be manufactured by methods known per se, for example in a manner analogous to that described in the Examples. The invention relates also to novel starting materials.

The pharmaceutical preparations according to the invention contain at least one compound of the general formula I or a salt thereof as the active substance together with a customary pharmaceutical carrier. The type of carrier depends largely on the field of use. The pharmaceutical compositions according to the invention which contain, as active substances, compounds of the formula I can be administered enterally, such as orally or rectally, parenterally, e.g. subcutaneously, intramuscularly or intravenously, or by inhalation.

For oral treatment, especially solid dosage unit forms, such as tablets, dragees and capsules are considered, which preferably contain between 10 and 90% of an active substance of the general formula I or a salt in order to allow administration to warm-blooded animals of daily doses of from 0.1 to 100 mg/kg, especially from 1 to 50 mg/kg. The daily dose depends on age and individual condition and also on the mode of administration. For the manufacture of tablets and dragee cores, the compounds of the general formula I are combined with solid, pulverulent carriers, such as lactose, saccharose, sorbitol, maize starch, potato starch or amylopectin, cellulose derivatives or gelatine, preferably with the addition of lubricants, such as magnesium or calcium stearate, or polyethylene glycols of a suitable molecular weight. Dragee cores are subsequently coated, for example with concentrated sugar solutions which may contain, in addition, gum arabic, talc and/or titanium dioxide, or with a lacquer dissolved in readily volatile organic solvents or solvent mixtures. Colouring substances can be added to these coatings, for example for indicating different doses of active substance. Soft gelatine capsules and other closed capsules consist, for example, of a mixture of gelatine and glycerin and may contain, for example, mixtures of a compound of the formula I and polyethylene glycol. Dry-filled capsules contain, for example, granules of an active substance with solid, pulverulent carriers, such as, for example, lactose, saccharose, sorbitol, mannitol; starches, such as potato starch, maize starch or amylopectin, cellulose derivatives and gelatine and also magnesium stearate or stearic acid.

Unit dosage forms that come into consideration for rectal administration are, for example, suppositories which consist of a combination of an active substance with a suppository base based on natural or synthetic triglycerides (for example cocoa butter), polyethylene glycols or suitable higher fatty alcohols, and gelatine rectal capsules which contain a combination of the active substance with polyethylene glycols.

Ampoule solutions for parenteral administration, especially for intramuscular or intravenous administration, contain a compound of the formula I or a salt thereof in a concentration of preferably 0.5 to 5% as an aqueous dispersion prepared with the aid of customary solubilisers and/or emulsifiers, and, optionally, stabilisers, or preferably as an aqueous solution of a pharmaceutically acceptable water-soluble salt of a compound of the general formula I.

For inhalation the active compound may be presented in association with volatile excipients, as a cream, lotion, paste or ointment or as a finely divided dry powder or in solution for inhalation through a nasal spray, atomiser or insufflator.

Inhalation preparations for the treatment of the respiratory tract by nasal, buccal or intrapulmonary administration are e.g. aerosols or sprays that can disperse the pharmacological active ingredient in the form of a powder or in the form of drops of a solution or suspension. Preparations having powder-dispersing properties generally contain, apart from the active ingredient, a liquid propellant gas having a boiling point of below room temperature and, if desired, carriers, such as liquid or solid, non-ionic or anionic surface-active agents and/or solid diluents. Preparations in which the pharmacological active ingredient is in solution, contain, in addition, a suitable propellant, and also, if necessary, an additional solvent and/or a stabiliser. Instead of the propellant gas, it is also possible to use compressed air, and this can be produced as required by means of a suitable compression and release device.

The concentration of the active substance for liquids that are to be taken orally, such as syrups or elixirs, is so selected that a single dose can easily be measured, for example as the contents of a teaspoon or a measuring spoon of, for example, 5 ml, or also as a multiple of that volume.

The following Examples (a) to (c) are intended to illustrate the manufacture of some typical forms of administration, but do not in any way represent the only embodiments of those forms of administration.

(a) 250 g of active substance are mixed with 550 g of lactose and 292 g of potato starch, and the mixture is moistened with an alcoholic solution of 8 g of gelatine and granulated by being passed through a sieve. After drying, 60 g of talc, 10 g of magnesium stearate and 20 g of colloidal silica are added and the mixture is pressed to form 10,000 tablets each weighing 119 mg and each containing 25 mg of active substance, which may, if desired, be provided with dividing notches of a finer adjustment of the dosage.

(b) A granulate is prepared from 100 g of active substance, 379 g of lactose and the alcoholic solution of 6 g of gelatine, which, after being dried, is mixed with 10 g of colloidal silica, 40 g of talc, 60 g of potato starch and 5 g of magnesium stearate and pressed to form 10,000 dragee cores. These are subsequently coated with a concentrated syrup consisting of 533.5 g of crystalline saccharose, 20 g of shellac, 75 g of gum arabic, 250 g of talc, 20 g of colloidal silica and 1.5 g of colouring substance, and dried. The resulting dragees each weight 150 mg and each contain 10 mg of active substance.

(c) 25 g of active substance and 1975 g of finely ground suppository base (for example, cocoa butter) are thoroughly mixed and then melted. 1000 suppositories of 2 g are cast from the melt which has been kept homogenous by stirring. They each contain 25 mg of active substance.

The following Examples serve to illustrate the invention but are not intended to limit the scope thereof in any way. Temperatures are given in degrees Centigrade. Unless defined otherwise, the evaporation of solvents is carried out under reduced pressure, for example between approximately 0.1 and 20 mbar.

EXAMPLE 1

A solution of 30 g flavanone in 150 ml dimethylformamide is prepared under nitrogen and cooled with an ice bath. 36 ml phosphorous oxychloride is added slowly over half an hour. The reaction is allowed to stand at room temperature for 15 hours. Then, the brown solution is poured slowly on a cooled saturated sodium acetate aqueous solution and stirring is maintained for fifteen minutes. The yellow precipitate which formed is dissolved with 400 ml methylene chloride and the aqueous layer is extracted with methylene chloride. The organic solutions are combined, washed with a saturated sodium bicarbonate aqueous solution, then with water, dried over magnesium sulfate, filtered and evaporated to dryness. The residual solid is recrystallised in normal hexane, and pure yellow crystalline 4-chloro-3-formyl-flav-3-ene is obtained; m.p. 112°–114° C.

EXAMPLE 2

As in example 1, but using 23 g thioflavanone, 115 ml dimethylformamide and 46 ml phosphorous oxychloride. Reaction time is only 4 hours. After hydrolysis and work up a residual yellow oil is obtained which is purified by preparative HPLC. The pure yellow oil obtained crystallised after a few days in yellow crystalline 4-chloro-3-formyl-thioflav-3-ene; m.p. 63°–65° C.

EXAMPLE 3

As in example 1, but using 2.4 g 5-hydroxy-flavanone, 20 ml dimethylformamide and 2.8 ml phosphorous oxychloride. Reaction time is forty hours at 75° C. After hydrolysis and usual work up the residual solid is purified by column chromatography. The best fractions are recrystallised in a mixture of toluene and hexane to give pure yellow crystalline 4-chloro-3-formyl-5-hydroxy-flav-3-ene; m.p. 165° C.

EXAMPLE 4

As in example 1, but using 10 g 6-fluoro-flavanone, 100 ml dimethylformamide and 15 ml phosphorous oxychloride. Reaction time is one hour and a half at 50° C. After hydrolysis a precipitate formed which is filtered, washed with water and dried over phosphorous pentoxyde. The residual solid is recrystallised in hexane and pure yellow crystalline 4-chloro-6-fluoro-3-formyl-flav-3-ene is obtained; m.p. 74°–75° C.

EXAMPLE 5

As in example 1, but using 6 g 6-carboxy-flavanone, 60 ml dimethylformamide and 15 ml phosphorous oxychloride. Reaction time is three hours at 50° C. After hydrolysis a precipitate formed which is filtered, washed with water and dried over phosphorous pentoxyde. The residual solid is dissolved in a 10% sodium bicarbonate aqueous solution, which is then washed with methylene chloride. The aqueous phase is acidified with a 10% hydrochloric acid solution and the precipitate which formed is filtered, washed and dried. The residual solid is recrystallised in a mixture of hexane and ethyl acetate and pure 6-carboxy-4-chloro-3-formyl-flav-3-ene is obtained; m.p. 262°–267° C.

EXAMPLE 6

As in example 1, but using 30 g 6-methyl-thioflavanone, 150 ml and 44 ml phosphorous oxychloride. Reaction time is one hour at 50° C. After hydrolysis and work up the residual yellow oil is crystallised in ethanol to give yellow crystalline 4-chloro-3-formyl-6-methyl-thioflav-3-ene; m.p. 97° C.

EXAMPLE 7

As in example 1, but using 10 g 7-fluoro-flavanone, 100 ml dimethylformamide and 15 ml phosphorous oxychloride. Reaction time is one hour and a half at 50° C. After hydrolysis and usual work up, the residual solid is recrystallised in hexane. Pure yellow crystalline 4-chloro-7-fluoro-3-formyl-flav-3-ene is obtained; m.p. 110°–112° C.

EXAMPLE 8

A solution of 1 g 7-N,N-dimethylamino-flavanone in 10 ml methylene chloride and 0.6 ml dimethylformamide is prepared under nitrogen and cooled with an ice bath. 0.7 ml phosphorous oxychloride is added slowly. The reaction is allowed to stand at room temperature for one hour. The hydrolysis is realised by addition of 100 ml of a 10% sodium acetate aqueous solution and stirring is maintained for fifteen minutes. After extraction with methylene chloride the organic phase is washed with water and dried over magnesium sulfate, filtered and evaporated to dryness. The residual oil is purified by column chromatography and the best fractions recrystallised in a mixture of toluene and hexane to give pure crystalline 4-chloro-7-N,N-dimethylamino-3-formyl-flav-3-ene; m.p. 152°–154° C.

EXAMPLE 9

A suspension of 3 g 7-acetylamino-3-N,N-dimethylaminomethylidene-flavanone in 30 ml methylene chloride is stirred under nitrogen. 4.1 ml phosphorous oxychloride is added slowly and solubilisation occurred. After half an hour stirring, the reaction mixture is cooled at 4° C. and 100 ml of a saturated sodium acetate solution is added. This mixture is extracted with methylene chloride and the organic phase is washed with water, dried over magnesium sulfate and evaporated to dryness. The residual brown solid is purified by column chromatography and the best fractions are recrystallised in a mixture of hexane and ethylacetate. Pure crystalline yellow 7-acetylamino-4-chloro-3-formyl-flav-3-ene is obtained; m.p. 188°–195° C.

EXAMPLE 10

As in example 1, but using 10 g 3'-fluoro-flavanone, 100 ml dimethylformamide and 15 ml phosphorous oxychloride. Reaction time is two hours at 50° C. After hydrolysis a precipitate formed which is filtered, washed with water and dried over phosphorous pentoxyde. The residual solid is recrystallised in a mixture of ethanol and water and pure yellow crystalline 4-chloro-3'-fluoro-3-formyl-flav-3-ene is obtained; m.p. 97°–99° C.

EXAMPLE 11

As in example 1, but using 25 g 4'-hydroxy-flavanone, 80 ml dimethylformamide and 38 ml phosphorous oxychloride. Reaction time is eighteen hours at room temperature. After hydrolysis and usual work up, the residual solid is purified by preparative HPLC to give after recrystallisation in 1,2-dichloroethane pure 4-chloro-3-formyl-4'-hydroxy-flav-3-ene; m.p. 176°–178.5° C.

EXAMPLE 12

As in example 11, but during purification of the residual solid by preparative HPLC other fractions are collected and recrystallised in a mixture of hexane and acetone to give pure crystalline 4-chloro-3-formyl-4'-formyloxy-flav-3-ene; m.p. 172°–174° C.

EXAMPLE 13

As in example 1, but using 5 g 5,7-dimethoxy-flavanone, 50 ml dimethylformamide and 6 ml phosphorous oxychloride. Reaction time is two hours at 50° C. After hydrolysis and work up the residual solid is purified by preparative HPLC and the corresponding fractions are recrystallised in diisopropylether. 4-chloro-5,7-dimethoxy-3-ormyl-flav-3-ene is obtained as yellow crystals; m.p. 143°–145° C.

EXAMPLE 14

As in example 1, but using 5 g 5,7-dimethoxy-flavanone, 50 ml dimethylformamide and 50 ml phosphorous oxychloride. Reaction time is one hour and a half at 100° C. After hydrolysis and usual work up, the residual brown solid is purified by column chromatography and the best fractions are recrystallised in a mixture of hexane and toluene. 4-chloro-3,8-diformyl-5,7-dimethoxy-flav-3-ene is obtained as yellow crystals; m.p. 189°–191° C.

EXAMPLE 15

As in example 1, but using 15 g 5,6,7-trimethoxyflavanone, 150 ml dimethylformamide and 26 ml phosphorous oxychloride. Reaction time is forty eight hours at room temperature. After hydrolysis and usual work up, the residual solid is purified by preparative HPLC and the best fractions are crystallised in hexane. 4-chloro-3-formyl-5,6,7-trimethoxyflav-3-ene is obtained as yellow crystals; m.p. 84°–87° C.

EXAMPLE 16

As in example 1, but using 30 g flavanone, in 400 ml methylene chloride, 23 ml dimethylformamide and 27 ml phosphorous oxychloride. Reaction time is two hours under reflux conditions. After hydrolysis, work up and recrystallisation in hexane, pure yellow crystalline 4-chloro-3-formyl-flav,-3-ene is obtained; m.p. 112°–114° C.

EXAMPLE 17

A solution of 2.8 g 3-N,N-dimethylaminomethylideneflavanone in 7 ml dichloromethane is cooled to 4° C. under nitrogen. 2 ml phosphorous oxychloride is slowly added and stirring is maintained while the temperature is allowed to rise to 20° C. Slow addition of 12 ml of a saturated sodium acetate aqueous solution is followed by extraction with methylene chloride. The organic phase is washed with water, dried over magnesium sulfate, filtered and evaporated to dryness. Pure 4-chloro-3-formyl-flav-3-ene is obtained as yellow crystals; m.p. 112°–114° C.

EXAMPLE 18

A mixture of 1.3 g 3-phenyl-3-phenylmercapto-propionic acid and 4ml phosphorous oxychloride is stirred under nitrogen at 70° C. for four hours. The reaction mixture is then cooled to 4° C. with an ice bath and 4 ml dimethylformamide is added. Stirring is maintained at room temperature for five hours. After cooling with an ice bath, 30 ml of a cooled saturated sodium acetate aqueous solution is added. After a few minutes stirring, the reaction mixture is extracted with methylene chloride, the organic layer washed with a saturated sodium bicarbonate aqueous solution then with water, dried over magnesium sulfate, filtered and evaporated to dryness. The residual oil is purified by column chromatography and pure yellow 4-chloro-3-formyl-thioflav-3-ene is obtained which crystallised after a few days; m.p. 63°–65° C.

EXAMPLE 19

As in example 17, but using 3 g 6-N,N-dimethylamino-3-N,N-dimethylaminomethylidene-flavanone, 30 ml methylene chloride and 4.3 ml phosphorous oxychloride. After recrystallisation in petroleum ether pure red crystalline 4-chloro-6-N,N-dimethylamino-3-formylflav-3-ene is obtained; m.p. 108°–110° C.

EXAMPLE 20

A solution of 1.35 g 4-chloro-3-formyl-flav-3-ene and 7.6 g cesium fluoride in 10 ml dimethylformamide is stirred at 110° C. over 40 minutes. After cooling to room temperature water is added and the solution is extracted with methylene chloride. The organic phase is washed with water, and dried over magnesium sulfate. The solid residue is purified by column chromatography and the best fractions are crystallised in hexane. Pure 4-fluoro-3-formyl-flav-3-ene is obtained as yellow crystals; m.p. 114°–115° C.

EXAMPLE 21

As in example 18, but using 4.3 g 3-phenyl-3-(3-methoxyphenylmercapto)propionic acid, 40 ml dimethylformamide and 15 ml phosphorous oxychloride. After hydrolysis and work-up the residual oil is purified by column chromatography and the best fractions are recrystallized in diisopropylether. Pure 4-chloro-3-formyl-7-methoxy-thioflav-3-ene is obtained as yellow crystals; m.p. 84°–87° C.

EXAMPLE 22

As in example 18,but using 4.3 g 3-phenyl-3-(2-methoxyphenylmercapto)propionic acid, 40 ml dimethylformamide and 15 ml phosphorous oxychloride. After hydrolysis and work-up the residual oil is filtered over a small silicagel column and the residual solid is recrystallized in a mixture of hexane and ethyl acetate. Pure 4-chloro-3-formyl-8-methoxy-thioflav-3-ene is obtained as yellow crystals; m.p. 128°–130° C.

EXAMPLE 23

As in example 18, but using 4.6 g 3-(4-fluorophenyl)-3-phenylmercapto-propionic acid, 40 ml dimethylformamide and 15 ml phosphorous oxychloride. After hydrolysis and work-up a residual oil is obtained which is purified by preparative HPLC. The oily fractions are crystallized in hexane and pure 4-chloro-4'-fluoro-3-formyl-thio-flav-3-ene is obtained as yellow crystals; m.p. 67°–69° C.

EXAMPLE 24

As in example 18, but using 5.4 g 3-(2-fluorophenyl)-3-phenylmercapto-propionic acid, 40 ml dimethylformamide and 15 ml phosphorous oxychloride. After hydrolysis a precipitate forms which is filtered, washed with water and dried over phosphorous pentoxide. The residual solid is recrystallized in hexane and pure yellow crystalline 4-chloro-2'-fluoro-3-formyl-thioflav-3-ene is obtained; m.p. 119°–120° C.

EXAMPLE 25

As in example 1, but using 2.2 g flavan-3-one, 12 ml dimethylformamide and 3 ml phosphorous oxychloride. Reaction time is one hour at 0°–5°. After hydrolysis and usual work up the residual oil is purified by column chromatography. The best fractions give a pale yellow oil of pure 3-chloro-4-formyl-flav-3-ene. TLC (n-hexane/acetone 4:1, SiO$_2$) single spot, R$_f$=0.47. NMR (90 MHz, CDCl$_3$):δ(ppm)=5.86 [1H, s, H-C(2)]; 6.7–7.5 [3H, m, H-C (6,7,8)]; 7.35 [5H, S,C$_6$H$_5$]; 8.15 [1H, dd, H-C(5)].

BEISPIEL 26

As in example 1, but using 0.34 g 5,7,3',4'-tetrasmethoxy-flavan-3-one and 1.5 ml dimethylformamide and 0.23 ml phosphorous oxychloride. Reaction time is 14 hours at 0°. After hydrolysis and usual work up the residual oil is purified by column chromatography on silica gel using diisopropylether as eluant. The best fractions are recrystallized in diisopropylether. Pure 3-chloro-4-formyl-5,7,3',4'-tetramethoxy-flav-3-ene is obtained as white crystals; m.p. 104°–105° C.

What is claimed is:

1. A compound of the formula

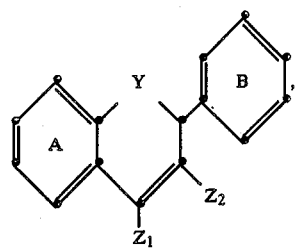

(I)

wherein rings A and B are each unsubstituted or substituted by 1, 3, or 4 substituents selected from the group consisting of lower alkyl, hydroxy, lower alkoxy, lower alkanoyloxy, lower alkylthio, amino, lower alkylamino, di-lower alkylamino, acylamino, halogen, carboxy, lower alkoxycarbonyl, carbamoyl, N-mono- or N,N-di-lower-alkylcarbamoyl, cyano, nitro, sulfo, sulfamoyl, N-lower-alkyl-, N,N-di-lower-alkyl- or N-phenylsulfamoyl, formyl and methylenedioxy; Y is oxygen, sulfur, sulfinyl or sulfonyl; one of the symbols $Z_1$ and $Z_2$ is halogen and the other formyl; and salts of such compounds that contain a salt-forming group.

2. A compound of claim 1 wherein Y is oxygen.

3. A compound of claim 1 wherein $Z_2$ is formyl and $Z_1$ is chloro.

4. A compound of claim 3 wherein Y is oxygen.

5. The compound of claim 1 which is 4-chloro-3-formyl-flav-3-ene.

6. The compound of claim 1 which is 4-chloro-3-formyl-thioflav-3-ene.

7. The compound of claim 1 which is 3-chloro-4-formyl-flav-3-ene.

8. A compound of the formula I according to claim 1, wherein rings A and B are each unsubstituted or substituted by 1, 2 or 3 substituents selected from the group consisting of lower alkyl, hydroxy, lower alkoxy, lower alkanoyloxy, lower alkylamino, di-lower alkylamino, lower alkanoylamino, halogen, formyl and carboxy; Y is oxygen or sulfur; one of the symbols $Z_1$ and $Z_2$ is chlorine or fluorine and the other is formyl; and pharmaceutically acceptable salts of such compounds that contain a salt-forming group.

9. A compound of formula I according to claim 1 being 4-chloro-3-formyl-5-hydroxy-flav-3-ene and pharmaceutically acceptable salts thereof.

10. A compound of formula I according to claim 1 being 4-chloro-6-fluoro-3-formyl-flav-3-ene.

11. A compound of formula I according to claim 1 being 6-carboxy-4-chloro-3-formyl-flav-3-ene and pharmaceutically acceptable salts thereof.

12. Pharmaceutical preparations containing a compound of formula I according to claim 1 or a pharmaceutically acceptable salt of such a compound that contains a salt-forming group and a pharmaceutically acceptable carrier.

13. A method of treating diseases of the respiratory tract in mammals comprising administering to a mammal in need thereof a therapeutically effective amount of a compound of formula I or a pharmaceutically acceptable salt thereof; said formula I being

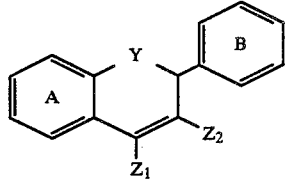

(I)

wherein
Y is oxygen, sulfur, sulfinyl, or sulfonyl; one of $Z_1$ and $Z_2$ is halogen and the other is formyl; and
rings A and B are each unsubstituted or substituted by 1, 2, 3, or 4 substituents selected from the group consisting of lower alkyl, hydroxy, lower alkoxy, lower alkanoyloxy, lower alkylthio, amino, lower alkylamino, di lower alkyl amino, acylamino, halogen, carboxy, lower alkoxycarbonyl, carbamoyl, N-mono-lower alkyl carbamoyl, N, N-di-lower alkyl carbamoyl, cyano, nitro, sulfo, sulfamoyl, N-lower alkyl sulfamoyl, N, N-di-lower alkyl sulfamoyl, N-phenyl sulfamoyl, formyl, and methylenedioxy.

14. A method of treating a liver disease in a mammal comprising administering to a mammal in need thereof a therapeutically effective amount of a compound of formula I or a pharmaceutically acceptable salt thereof; said formula I being

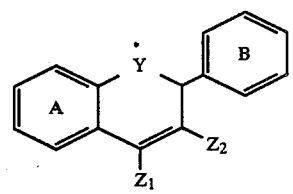

(I)

wherein
Y is oxygen, sulfur, sulfinyl, or sulfonyl; one of $Z_1$ and $Z_2$ is halogen and the other is formyl; and
rings A and B are each unsubstituted or substituted by 1, 2, 3, or 4 substituents selected from the group consisting of lower alkyl, hydroxy, lower alkoxy, lower alkanoyloxy, lower alkylthio, amino, lower alkylamino, di lower alkyl amino, acylamino, halogen, carboxy, lower alkoxycarbonyl, carbamoyl, N-mono-lower alkyl carbamoyl, N,N-di-lower alkyl carbamoyl, cyano, nitro, sulfo, sulfamoyl, N-lower alkyl sulfamoyl, N,N-di-lower alkyl sulfamoyl, N-phenyl sulfamoyl, formyl, and methylenedioxy.

15. A method of stimulating an immunologic defense in a mammal comprising administering to a mammal in need thereof a therapeutically effective amount of a compound of formula I or a pharmaceutically acceptable salt thereof; said formula I being

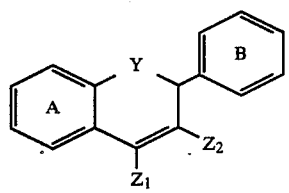

(I)

wherein
Y is oxygen, sulfur, sulfinyl, or sulfonyl; one of $Z_1$ and $Z_2$ is halogen and the other is formyl; and rings A and B are each unsubstituted or substituted by 1, 2, 3, or 4 substituents selected from the group consisting of lower alkyl, hydroxy, lower alkoxy, lower alkanoyloxy, lower alkylthio, amino, lower alkylamino, di lower alkyl amino, acylamino, halogen, carboxy, lower alkoxycarbonyl, carbamoyl, N-mono lower alkyl carbamoyl, N,N-di-lower alkyl carbamoyl, cyano, nitro, sulfo, sulfamoyl, N-lower alkyl sulfamoyl, N, N-di-lower alkyl sulfamoyl, N-phenyl sulfamoyl, formyl, and methylenedioxy.

* * * * *